US00PP13810P29

(12) United States Plant Patent
Smith

(10) Patent No.: US PP13,810 P2
(45) Date of Patent: May 13, 2003

(54) CHRYSANTHEMUM PLANT NAMED 'YOALBERTA'

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/094,338

(22) Filed: Mar. 8, 2002

(51) Int. Cl.[7] ..... A01H 5/00
(52) U.S. Cl. ..... Plt./287

(58) Field of Search ..... Plt./287

*Primary Examiner*—Bruce R. Campell
*Assistant Examiner*—Annette H. Para
(74) *Attorney, Agent, or Firm*—C. A. Whealy

(57) ABSTRACT

A distinct cultivar of Chrysanthemum plant named 'Yoalberta', characterized by its upright and outwardly spreading plant habit; freely branching habit; uniform and freely flowering habit; decorative-type inflorescences with quilled ray florets; dark orange-colored ray florets; and natural season flowering in early October in the Northern Hemisphere.

1 Drawing Sheet

BOTANICAL CLASSIFICATION/CULTIVAR DESIGNATION

*Crysanthemum×morifolium* cultivar Yoalberta.

BACKGROUND OF THE INVENTION

The present invention relates to a new and distinct cultivar of Chrysanthemum plant, botanically known as *Chrysanthemum×morifolium*, commercially known as a garden-type Chrysanthemum and hereinafter referred to by the name 'Yoalberta'.

The new cultivar is a product of a planned breeding program conducted by the Inventor in Salinas, Calif. and Fort Myers, Fla. The objective of the breeding program is to create new garden-type Chrysanthemum cultivars having inflorescences with desirable inflorescence forms, attractive floret colors and good garden performance.

The new Chrysanthemum originated from a cross made in November, 1993, in Salinas, Calif., of the Chrysanthemum cultivar Sarah, disclosed in U.S. Plant Pat. No. 7,586, as the female, or seed, parent with an unnamed Chrysanthemum proprietary seedling selection, not patented, as the male, or pollen, parent. The new Chrysanthemum was discovered and selected by the Inventor as a single flowering plant within the progeny of the stated cross grown in a controlled environment in Fort Myers, Fla. in October, 1998. The selection of this plant was based on its desirable inflorescence form, attractive ray floret color and good garden performance.

Asexual reproduction of the new cultivar by terminal cuttings taken in a controlled environment in Fort Myers, Fla. since January, 1999, has shown that the unique features of this new Chrysanthemum are stable and reproduced true to type in successive generations.

SUMMARY OF THE INVENTION

The cultivar Yoalberta has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoalberta'. These characteristics in combination distinguish 'Yoalberta' as a new and distinct cultivar:

1. Upright and outwardly spreading plant habit.
2. Freely branching habit; dense and full plants.
3. Uniform and freely flowering habit.
4. Decorative-type inflorescences with quilled ray florets.
5. Dark orange-colored ray florets.
6. Natural season flowering in early October in the Northern Hemisphere.

Plants of the new Chrysanthemum are most similar to plants of the female parent, the cultivar Sarah. In side-by-side comparisons conducted in Fort Myers, Fla., plants of the new Chrysanthemum differed from plants of the cultivar Sarah in the following characteristics:

1. Plants of the new Chrysanthemum were not as upright and had a more uniform plant habit than plants of the cultivar Sarah.
2. Plants of the new Chrysanthemum flowered more uniformly than plants of the cultivar Sarah.
3. Plants of the new Chrysanthemum had smaller inflorescences than plants of the cultivar Sarah.
4. Plants of the new Chrysanthemum flowered a few days earlier than plants of the cultivar Sarah.
5. Ray florets of the new Chrysanthemum and the cultivar Sarah differed in color as ray florets of the cultivar Sarah were yellow bronze.

In side-by-side comparisons conducted in Fort Myers, Fla., plants of the new Chrysanthemum differed from plants of the male parent, the unnamed selection, in the following characteristics:

1. Inflorescences of the new Chrysanthemum had quilled ray florets whereas inflorescences of the male parent did not have quilled ray florets.
2. Inflorescences of the new Chrysanthemum had few to no disc florets whereas inflorescences of the male parent had numerous disc florets.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Yoalberta'.

The photograph at the bottom of the sheet comprises a close-up view of typical inflorescences of the cultivar 'Yoalberta'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in an outdoor nursery in Pendleton, S.C., under natural season conditions and practices which approximate those generally used in commercial garden-type Chrysanthemum production. One rooted cutting was planted in a 16.5-cm container in late July, 2002. Plants were not pinched, that is, the terminal apex was not removed to enhance branching. During the production of the plants, day temperatures ranged from 29 to 32° C. and night temperatures ranged from 16 to 21° C. Measurements and numerical values represent averages for typical flowering plants.

Botanical classification: *Chrysanthemum×morifolium* cultivar Yoalberta.

Commercial classification: Decorative-type garden Chrysanthemum.

Parentage:

*Female, or seed, parent.*—*Chsysanthemum× morifolium* cultivar Sarah, disclosed in U.S. Plant Pat. No. 7,586.

*Male, or pollen, parent.*—Unnamed *Chrysanthemum× morifolium* proprietary seedling selection, not patented.

Propagation:

*Type.*—Terminal tip cuttings.

*Time to initiate roots.*—About four days at 21° C.

*Time to produce a rooted cutting.*—About ten days at 21° C.

*Root description.*—White, fine and fibrous.

*Rooting habit.*—Freely branching.

Plant description:

*Appearance.*—Perennial herbaceous decorative-type garden Chrysanthemum. Inverted triangle; stems mostly upright and somewhat outwardly spreading giving a uniformly mounded to flat-top appearance to the plant. Freely branching with lateral branches forming at every node.

*Plant height.*—About 30.5 cm.

*Plant diameter.*—About 39 cm.

*Lateral branches.*—Length: About 27 cm. Diameter: About 5 mm. Internode length: About 2.4 cm. Aspect: Mostly upright and somewhat outwardly spreading. Texture: Pubescent. Color: 146A.

*Foliage description.*—Leaf arrangement: Alternate. Length: About 5 cm. Width: About 4.5 cm. Apex: Cuspidate to mucronate. Base: Truncate. Margin: Palmately lobed, sinuses mostly parallel. Texture: Both surfaces, pubescent; veins prominent on lower surface. Color: Young and fully expanded foliage upper surface: Slightly darker than 147A. Young and fully expanded foliage lower surface: Slightly darker than 147B. Venation, upper and lower surfaces: 147B. Petiole length: About 2.2 cm. Petiole diameter: About 2.5 mm. Petiole color, upper surface: Close to 147B. Petiole color, lower surface: Close to 147B to 147C.

Inflorescence description:

*Appearance.*—Decorative-type inflorescence form with quilled ray florets. Inflorescences borne on terminals above foliage, arising from leaf axils. Disk and ray florets arranged acropetally on a capitulum. About 4 or 5 inflorescences per lateral.

*Flowering response.*—Under natural season conditions, plants flower in early October in the Northern Hemisphere and continue to flower for at least three weeks depending on weather conditions.

*Inflorescence bud (before showing color).*—Height: About 5 mm. Diameter: About 6 mm. Phyllary color: Darker than 143A.

*Inflorescence size.*—Diameter: About 4.8 cm. Depth (height): About 2.3 cm. Disc diameter: About 2 mm or less, inconspicuous. Receptacle diameter: About 5 mm.

*Ray florets.*—Shape: Quilled. Length: About 2.8 cm. Corolla tube length: About 2.7 cm. Width: About 3 mm. Apex: Acute, emarginate or rounded. Margin: Fused, no margin. Texture: Smooth, glabrous, satiny. Surface: Mostly flat. Orientation: Initially upright, then about 45° from vertical. Number of ray florets per inflorescence: About 215. Color: When opening, upper and lower surfaces: Close to 171A. Opened inflorescence, upper surface (throat): 169A to 34A; fading to close to 169B with subsequent development. Opened inflorescence, lower surface (tube): 160A faintly overlain with 169A to 34A; fading to lighter han 169A with subsequent development.

*Disc florets.*—Shape: Tubular, apex dentate. Length: About 3 mm. Width: Apex: About 1 mm. Base: About 1 mm. Number of disc florets per inflorescence: None or less than 10. Color: Immature: 154A to 9A. Mature: Apex: 9A. Mid-section: 154D. Base: 155D.

*Peduncle.*—Aspect: Flexible, angled about 45° from the stem. Length: First peduncle: About 5.4 cm. Fourth peduncle: About 6.7 cm. Diameter: About 2.5 mm. Texture: Pubescent. Color: 146A.

*Reproductive organs.*—Androecium: Present on disc florets only. Anther color: 9A. Pollen: None observed. Gynoecium: Present on both ray and disc florets.

*Seed.*—Seed production has not been observed.

Disease/pest resistance: Plants of the new Chrysanthemum have not been shown to be resistant to pathogens and pests common to Chrysanthemums.

Garden performance: Plants of the new Chrysanthemum have been observed to be tolerant to rain, wind and temperatures ranging from 0 to more than 40° C.

It is claimed:

1. A new and distinct cultivar of Chrysanthemum plant named 'Yoalberta', as illustrated and described.

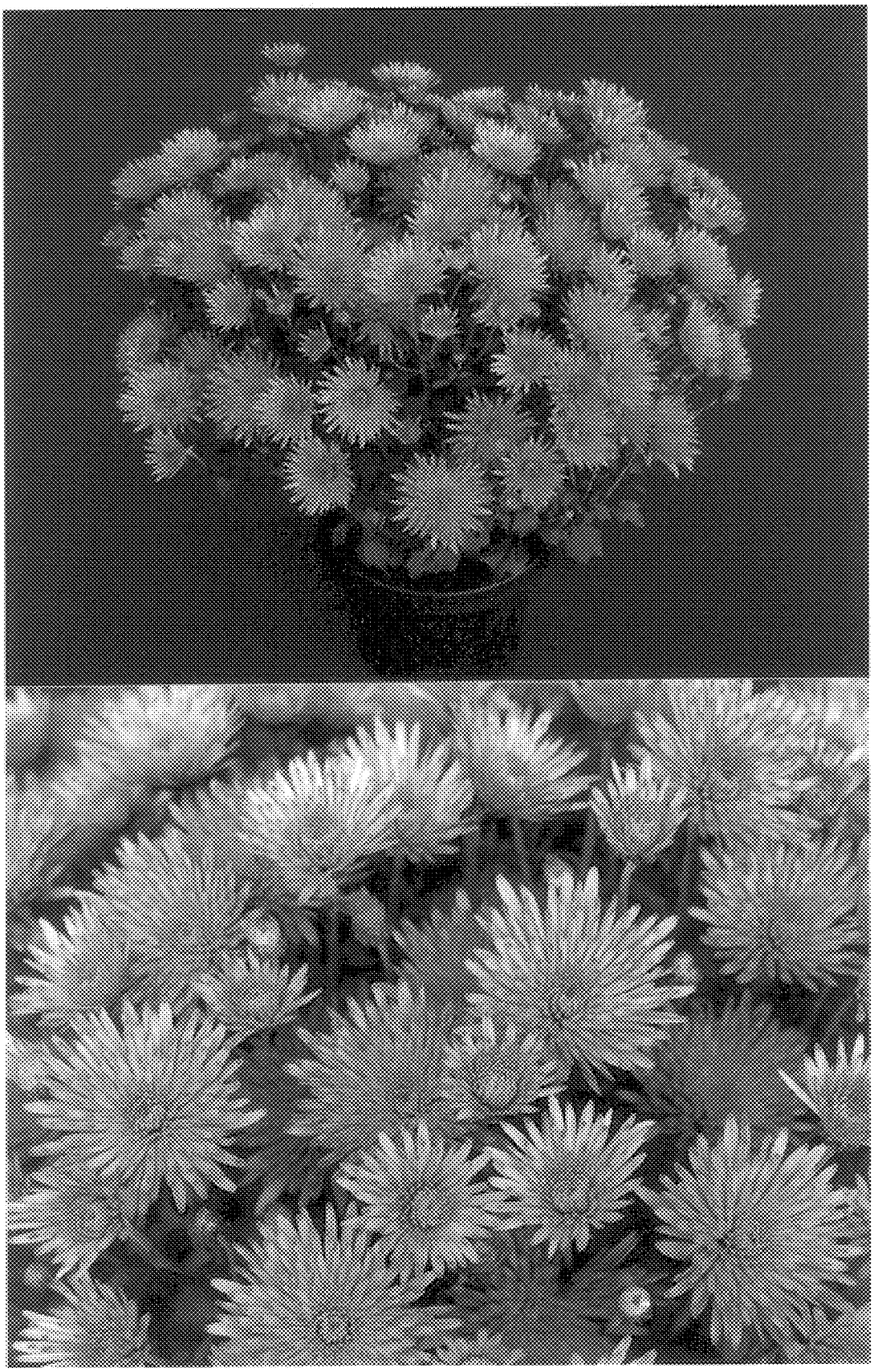

* * * * *